(12) United States Patent
Watson et al.

(10) Patent No.: US 11,844,624 B2
(45) Date of Patent: Dec. 19, 2023

(54) SYSTEM AND METHOD FOR MONITORING CEREBRAL ACTIVITY

(71) Applicant: Covidien LP, Mansfield, MA (US)

(72) Inventors: James N. Watson, Edinburgh (GB); Paul S. Addison, Edinburgh (GB)

(73) Assignee: COVIDIEN LP, Mansfield, MA (US)

(*) Notice: Subject to any disclaimer, the term of this patent is extended or adjusted under 35 U.S.C. 154(b) by 474 days.

(21) Appl. No.: 17/029,965

(22) Filed: Sep. 23, 2020

(65) Prior Publication Data

US 2021/0000413 A1  Jan. 7, 2021

Related U.S. Application Data

(62) Division of application No. 14/993,856, filed on Jan. 12, 2016, now Pat. No. 10,835,174.

(51) Int. Cl.
| A61B 5/00 | (2006.01) |
| A61B 5/369 | (2021.01) |
| A61B 5/1455 | (2006.01) |
| G16H 10/60 | (2018.01) |
| G16H 40/63 | (2018.01) |
| G16H 50/30 | (2018.01) |

(52) U.S. Cl.
CPC ........ *A61B 5/4821* (2013.01); *A61B 5/14551* (2013.01); *A61B 5/369* (2021.01); *A61B 5/7221* (2013.01); *G16H 10/60* (2018.01); *G16H 40/63* (2018.01); *G16H 50/30* (2018.01)

(58) Field of Classification Search
None
See application file for complete search history.

(56) References Cited

U.S. PATENT DOCUMENTS

| 5,020,540 | A | 6/1991 | Chamoun |
| 5,458,117 | A | 10/1995 | Chamoun et al. |
| 5,902,235 | A | 5/1999 | Lewis et al. |
| 6,599,251 | B2 | 7/2003 | Chen et al. |
| 6,934,570 | B2 | 8/2005 | Kiani et al. |
| 7,407,485 | B2 | 8/2008 | Huiku |
| 7,407,486 | B2 | 8/2008 | Huiku |
| 8,821,397 | B2 | 9/2014 | Al-Ali et al. |
| 10,383,579 | B2 | 8/2019 | Addison et al. |

(Continued)

OTHER PUBLICATIONS

Bidd et al. "Using bispectral index and cerebral oximetry to guide hemodynamic therapy in high-risk surgical patients," Perioperative Medicine, May 2013, 9 pp.

(Continued)

*Primary Examiner* — Etsub D Berhanu
(74) *Attorney, Agent, or Firm* — Fletcher Yoder, P.C.

(57) ABSTRACT

A patient monitor for monitoring cerebral activity of a patient may include a processor configured to determine a depth of consciousness index for the patient based on electroencephalography (EEG) data and determine regional oxygen saturation for the patient based on regional oximetry data. Additionally, the processor may be configured to determine a metric associated with cerebral activity of the patient based at least in part on the one or more values of the depth of consciousness index and the one or more regional oxygen saturation values and to provide the one or more values of a depth of consciousness index and the metric to an output device.

15 Claims, 8 Drawing Sheets

(56) References Cited

U.S. PATENT DOCUMENTS

| 10,835,174 | B2 | 11/2020 | Watson et al. |
| 2004/0243017 | A1 | 12/2004 | Causevic |
| 2006/0129204 | A1 | 6/2006 | Pless et al. |
| 2006/0217614 | A1 | 9/2006 | Takala |
| 2006/0265002 | A1 | 11/2006 | John et al. |
| 2007/0010723 | A1 | 1/2007 | Uutela et al. |
| 2008/0188729 | A1 | 8/2008 | Sato et al. |
| 2008/0188760 | A1 | 8/2008 | Al-Ali et al. |
| 2008/0228053 | A1 | 9/2008 | Wang et al. |
| 2009/0326386 | A1 | 12/2009 | Sethi et al. |
| 2010/0177100 | A1 | 7/2010 | Carnes et al. |
| 2011/0105912 | A1 | 5/2011 | Widman et al. |
| 2011/0270047 | A1 | 11/2011 | O'Brien |
| 2012/0053433 | A1 | 3/2012 | Chamoun et al. |
| 2012/0083673 | A1* | 4/2012 | Al-Ali .................... A61B 5/374 600/301 |
| 2012/0203087 | A1 | 8/2012 | McKenna et al. |
| 2012/0203123 | A1* | 8/2012 | Mahajan ................ A61B 5/024 600/509 |
| 2013/0030267 | A1 | 1/2013 | Lisogurski et al. |
| 2013/0331660 | A1 | 12/2013 | Al-Ali et al. |
| 2014/0073888 | A1 | 3/2014 | Sethi et al. |
| 2014/0073930 | A1 | 3/2014 | Sethi et al. |
| 2014/0275816 | A1 | 9/2014 | Sandmore |
| 2017/0095161 | A1 | 4/2017 | Addison et al. |

OTHER PUBLICATIONS

Kanemaru, Yoshinori, et al.; "Bispectral index and regional cerebral oxygen saturation during propofoi/N20 anesthesia," Canadian Journal of Anesthesia, vol. 53, No. 4, Apr. 2006, pp. 363-396.

Zhang, Kai-ying, et al. .; "Influence of the depth of sedation on regional cerebral oxygen saturation monitoring in neurosurgery of supratentorial gliomas," Chinese Journal of Contemporary Neurology and Neurosurgery, vol. 12, No. D6, Dec. 2012, pp. 696-700.

Meng, L., et al.; "Changes in cerebral tissue oxygen saturation during anaesthetic-induced hypotension: an interpretation based on neurovascular coupling and cerebral autoregulation," Anesthesia, vol. 68, Apr. 2013, pp. 736-741.

\* cited by examiner

# SYSTEM AND METHOD FOR MONITORING CEREBRAL ACTIVITY

This application is a divisional of U.S. patent application Ser. No. 14/993,856, which was filed on Jan. 12, 2016, and is entitled, "SYSTEM AND METHOD FOR MONITORING CEREBRAL ACTIVITY," the entire content of which is incorporated herein by reference.

BACKGROUND

The present disclosure relates generally to medical devices and, more particularly, to patient monitoring systems for monitoring physiological parameters of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring certain physiological characteristics of a patient. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as electroencephalography (EEG), and the devices built based upon electroencephalographic techniques are commonly referred to as EEG monitors. EEG monitors use non-invasive electrophysiological monitoring to evaluate global changes in a patient's condition, for example, during surgical procedures. Examples of global changes may include assessing the effects of anesthetics. For example, certain techniques analyze EEG signals using various algorithms to measure the depth of consciousness (DOC) of a patient during general anesthesia.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
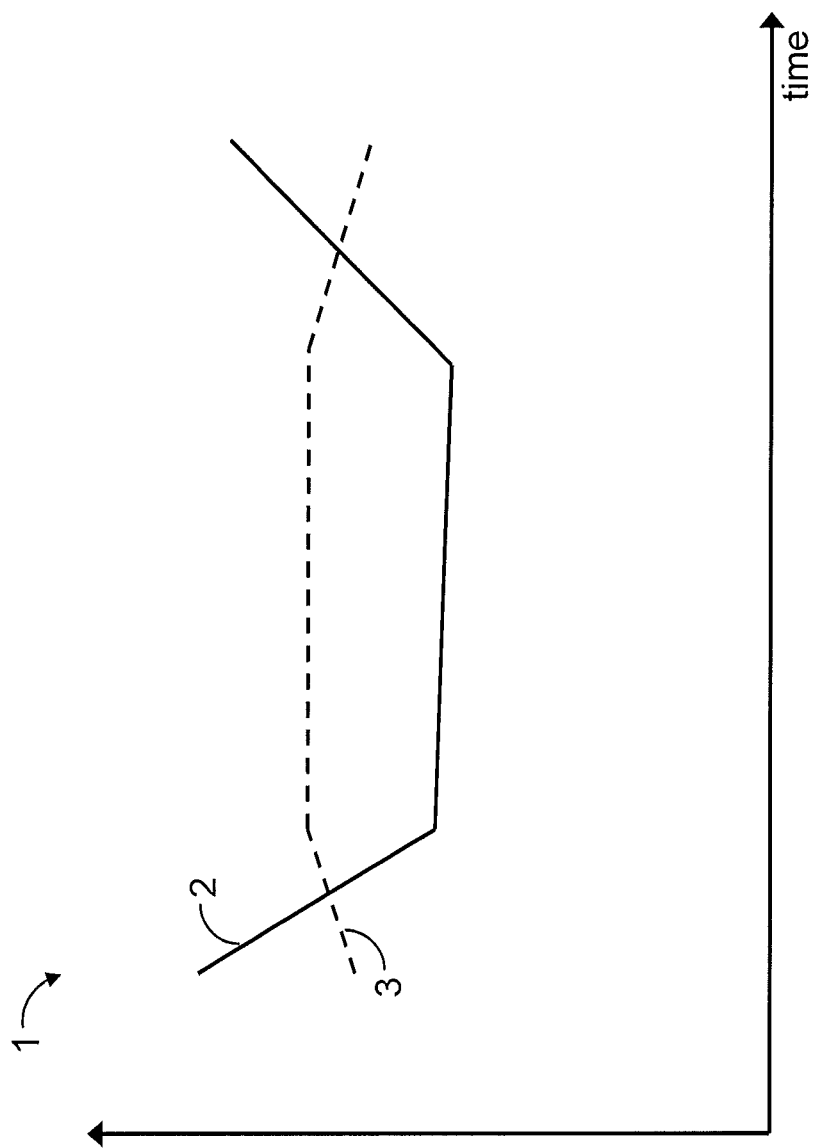
FIG. 1 is a plot of a patient's depth of consciousness index (DOCx) and regional oxygen saturation over time, in accordance with an embodiment.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Electroencephalography (EEG) monitors may be used in conjunction with EEG sensors to monitor a patient's cerebral activity. For example, an EEG monitor may analyze EEG signals from an EEG sensor to measure a patient's level or depth of consciousness (DOC) during general anesthesia used, for example, during a surgical procedure. The depth of consciousness index (DOCx) may provide useful information to a clinician to facilitate the monitoring and medical care of the patient. For example, the clinician may use the DOCx to assess the patient's condition and cerebral activity and to adjust a level of anesthetics provided to the patient. In some situations, the clinician may adjust the amount of anesthetics provided to the patient to maintain the patient's DOCx below a predetermined threshold or within a predetermined threshold range. For example, increasing EEG activity and an increasing DOCx may be associated with increasing awareness of the patient. As such, it may be desirable to maintain the patient's DOCx below a predetermined threshold or within a predetermined threshold range to minimize or reduce anesthesia awareness and recall. Thus, by using the DOCx, the clinician may be able to determine an appropriate amount of anesthetics for the patient while minimizing or reducing anesthesia awareness and recall.

Additionally, oxygen saturation monitors, such as regional oxygen saturation monitors, may be used in conjunction with regional oximetry sensors to monitor the oxygen saturation in a particular region of a patient's body. Such a measurement, referred to as regional saturation, is commonly used to monitor the oxygen saturation in a patient's brain when the patient is under anesthesia, for example, during a surgical procedure. Normal or expected values of regional oxygen saturation in the brain (e.g., cerebral oxygen saturation) may indicate that the patient is maintaining appropriate cerebral hemispheric blood oxygen saturation levels while under anesthesia. Deviation from normal values (e.g., a baseline value determined before induction of anesthesia) may alert a clinician to the presence of a particular condition. For example, oxygen desaturation in the patient's brain may indicate that the patient's brain is not sufficiently receiving oxygenated hemoglobin. Such an indication may enable the clinician to take necessary actions to prevent or reduce hypoxia in the brain, which may improve the patient's condition.

In some situations, the patient's regional oxygen saturation (e.g., cerebral oxygen saturation) may vary with the DOCx. For example, an increase in EEG activity (e.g., an increase in the DOCx) may also be associated with an increase in cerebral metabolic demand, which may cause a decrease in the patient's regional oxygen saturation (e.g., cerebral oxygen saturation). Similarly, a decrease in EEG activity (e.g., a decrease in the DOCx) may be associated with a decrease in cerebral metabolic demand, which may cause an increase in the patient's regional oxygen saturation. For example, FIG. 1 illustrates a plot 1 of a patient's DOCx values 2 and regional oxygen saturation values 3 over time. As illustrated, an increase in the DOCx values 2 is associated with a decrease in the regional oxygen saturation values 3, and a decrease in the DOCx values 2 is associated with an increase in the regional oxygen saturation values 3. Further, as illustrated, the regional oxygen saturation values 3 may remain generally stable (e.g., not positively trending or negatively trending) while the DOCx values 2 are generally stable. Thus, the regional oxygen saturation values 3 generally vary with the DOCx values 2 in an expected relationship. It should be appreciated that the plot 1 illustrates one possible relationship between the DOCx values 2 and the regional oxygen saturation values 3, and deviations from the illustrated relationship may be observed. For example, the relationship between DOCx and regional oxygen saturation may vary between patients, surgical procedures, anesthetic agents, etc.

As described in detail below, the systems and methods provided herein are directed toward techniques for monitoring a patient's cerebral activity based at least in part upon the DOCx and the regional oximetry saturation of the patient. In some embodiments, a monitor may be configured to analyze values of the DOCx and values of regional oxygen saturation for a period of time to determine a metric associated with the cerebral activity of the patient. For example, the metric may be a confidence level that is indicative of the accuracy and/or reliability of the DOCx. For example, the analysis may include determining a relationship between DOCx and regional oxygen saturation, such as a relationship between a change in DOCx values and a change in regional oxygen saturation values over a period of time, a relationship between a trend in DOCx values and a trend in regional oxygen saturation values over time, and/or a correlation between DOCx values and regional oxygen saturation values. Additionally, the analysis may include determining whether the determined relationship generally conforms to an expected relationship (e.g., negatively trending DOCx values are associated with positively trending regional oxygen saturation values, positively trending DOCx values are associated with negatively trending regional oxygen saturation values, etc.). For example, if the determined relationship generally conforms to an expected relationship, then the confidence level in the DOCx may be high. Conversely, if the determined relationship does not generally conform to an expected relationship, then the confidence level may be low.

While the patient's regional oxygen saturation may vary based on the metabolic demand, deviations in the regional oxygen saturation not associated with metabolic demand may occur if the patient is impaired. These deviations may occur, for example, due to a traumatic brain injury, an ischemic event, a stroke, or a seizure. As such, the patient's regional oxygen saturation may not provide accurate information to evaluate the DOCx (e.g., to determine the confidence level) while the patient is impaired.

Accordingly, certain embodiments include techniques for monitoring a patient's cerebral activity based at least in part upon the DOCx and cerebral autoregulation information of the patient. Cerebral autoregulation is a process that attempts to maintain an optimal blood flow to the brain during changes in blood pressure. If the cerebral autoregulation is impaired, it may indicate that the patient is impaired and that there may be deviations in the patient's regional oxygen saturation that are not associated with changes in metabolic demand. In certain embodiments, the monitor may utilize the cerebral autoregulation information to evaluate or qualify the metric (e.g., the confidence level). For example, the monitor may determine that the confidence level determined based on the DOCx and the patient's regional oxygen saturation may not be accurate or reliable if the cerebral autoregulation is impaired, because there may be deviations in the patient's regional oxygen saturation that are not associated with changes in metabolic demand.

Figure 2:
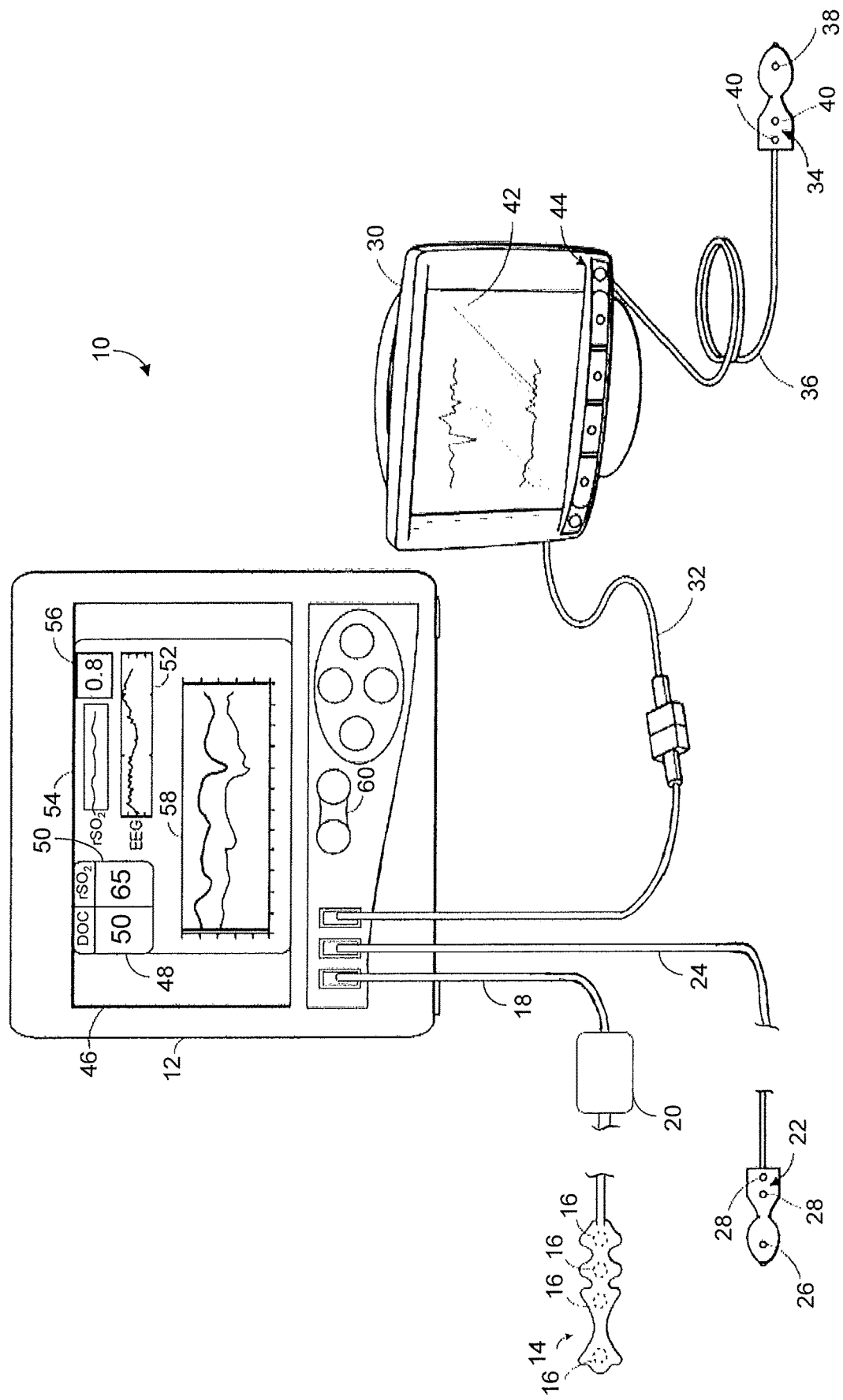
FIG. 2 is a perspective view of a patient monitoring system for monitoring cerebral activity of a patient using regional oximetry data, in accordance with an embodiment.

With the foregoing in mind, FIG. 2 illustrates an embodiment of a patient monitoring system 10 that includes an electroencephalography (EEG) monitor 12 that may be used in conjunction with an EEG sensor 14. The EEG sensor 14 may include electrodes 16 that are used to acquire EEG signals from a patient. While the illustrated embodiment of the EEG sensor 14 includes four electrodes 16, it should be appreciated that any number of electrodes 16 may be used, such as, for example, between 4 and 500 electrodes 16. The EEG signals acquired from the EEG sensor 14 may be used by the EEG monitor 12 to determine one or more physiological parameters of the patient. For example, the monitor 12 may determine a depth of consciousness index (DOCx) (e.g., a depth of anesthesia index or value) based at least in part on the EEG signals from the EEG sensor 14.

The EEG sensor 14 is communicatively coupled to the EEG monitor 12. Although only one EEG sensor 14 is shown coupled to the EEG monitor 12, in other embodiments, two, three, or more EEG sensors 14 may be coupled to the EEG monitor 12. The EEG sensor 14 may be coupled to the EEG monitor 12 via a cable 18. In some embodiments, the cable 18 may be coupled to a digital signal converter 20. The digital signal converter 20 may filter and process the EEG signals for each channel of the EEG sensor 14. In certain embodiments, the digital signal converter 20 may be embedded in the EEG monitor 12.

As noted above, the EEG monitor 14 may be configured to calculate physiological parameters based at least in part on the EEG signals from the EEG sensor 14. The EEG monitor 14 may include a memory storing computer-readable instructions and/or algorithms and a processor configured (e.g., programmed) to access the memory to read and execute the instructions and/or algorithms to implement the techniques described herein. For example, the EEG monitor 14 may be configured to determine a DOCx based at least in part on the EEG signals from the EEG sensor 14. In certain embodiments, the DOCx may be determined based at least in part on a bispectral analysis of the EEG signals. In some embodiments, the DOCx may be a BISPECTRAL™ index (e.g., a BIS™ value), which may be determined using the techniques discussed in U.S. Pat. No. 5,458,117, which is hereby incorporated by reference for all purposes. In some embodiments, the DOCx may be an EEG index, a Narcotrend™ index, an Alaris auditory evoked potential (AEP)

index (e.g., an AAI index or value), a Sedline™ patient state index (PSI™), an index of consciousness (IoC), a cerebral state index (CSI), or any other suitable index indicative of the depth of consciousness or depth of anesthesia of the patient. Additionally, as will be described in more detail below, the EEG monitor 14 may be configured to use regional oximetry data (e.g., cerebral oximetry data) of the patient to evaluate or qualify the DOCx, to determine a metric indicative of a relationship between the DOCx and the patient's regional oxygen saturation. In some embodiments, the metric may be a confidence level that is indicative of the accuracy and/or reliability of the DOCx.

Accordingly, the EEG monitor 14 may also be configured to receive and analyze regional oximetry data of the patient. For example, in certain embodiments, the EEG monitor 14 may be coupled to a regional oximetry sensor 22 configured to generate an oxygen saturation signal indicative of blood oxygen saturation within the venous, arterial, and capillary systems within a region of the patient. For example, the regional oximetry sensor 22 may be configured to be placed on the patient's forehead and may be used to calculate the regional oxygen saturation (e.g., cerebral oxygen saturation) of the patient's blood within the venous, arterial, and capillary systems of a region underlying the patient's forehead (e.g., in the cerebral cortex). While FIG. 2 illustrates one regional oximetry sensor 22 coupled to the EEG monitor 14, in other embodiments, two, three, four, or more regional oximetry sensors 22 may be used. Further, in certain embodiments, the regional oximetry sensor 22 and the EEG sensor 14 may be part of the same sensor or supported by a single sensor housing. The regional oximetry sensor 22 may be coupled to the EEG monitor 14 via a cable 24 or may wirelessly communicate with the EEG monitor 14.

The regional oximetry sensor 22 may include at least one emitter 26 and at least two detectors 28. The emitter 26 may include at least two light emitting diodes (LEDs), each configured to emit at different wavelengths of light, such as, for example, red or near infrared light. One of the detectors 28 may be positioned relatively "close" (e.g., proximal) to the emitter 26 and one of the detectors 28 may be positioned relatively "far" (e.g., distal) from the emitter 26. Light intensity of multiple wavelengths may be received at both the "close" and the "far" detectors 28. For example, if two wavelengths are used, the two wavelengths may be contrasted at each location, and the resulting signals may be contrasted to arrive at a regional oxygen saturation value that pertains to additional tissue through which the light received at the "far" detector 28 passed (e.g., tissue in addition to the tissue through which the light received by the "close" detector 28 passed, e.g., the brain tissue), when it was transmitted through a region of a patient (e.g., a patient's cranium). Surface data from the skin and skull may be subtracted out, to generate a regional oxygen saturation signal for the target tissues over time.

As discussed in more detail below, the regional oximetry sensor 14 may provide the regional oxygen saturation signal to the EEG monitor 12 or to any other suitable processing device to enable evaluation of the patient's DOCx and/or cerebral activity. For example, in some embodiments, the EEG monitor 12 may be configured to utilize a raw or processed regional oxygen saturation signal to evaluate the DOCx and/or to determine the metric. In other embodiments, the EEG monitor 12 may execute code (e.g., stored in a memory) to calculate regional oxygen saturation (e.g., cerebral oxygen saturation) from the regional oxygen saturation signal and may evaluate the DOCx and/or determine the metric based at least in part on the calculated regional oxygen saturation.

Additionally or alternatively, the EEG monitor 12 may receive a calculated regional oxygen saturation value. For example, the regional oximetry sensor 22 may be configured to calculate regional oxygen saturation and may provide the regional oxygen saturation value to the EEG monitor 12. In some embodiments, the EEG monitor 12 may receive calculated regional oxygen saturation values from a patient monitor 30. It should be noted that the patient monitor 30 may additionally or alternatively provide a raw or processed regional oxygen saturation signal to the EEG monitor 12. The patient monitor 30 may be coupled to the EEG monitor 12 via a cable 32 or may wirelessly communicate with the EEG monitor 12. For example, the patient monitor 30 may be a regional oximeter (e.g., a cerebral oximeter), a functional magnetic resonance imaging (fMRI) scanner, a positron emission tomography (PET) scanner, or any other device configured to provide a regional oxygen saturation signal and/or a calculated regional oxygen saturation value to the EEG monitor 12. Further, in some embodiments, the EEG monitor 12 and the patient monitor 30 may be an integrated monitor (e.g., disposed in the same housing).

The patient monitor 30 may also be communicatively coupled to a regional oximetry sensor 34. In particular, the regional oximetry sensor 34 may be coupled to the patient monitor 30 via a cable 36 or may communicate wirelessly with the patient monitor 30. Similar to the regional oximetry sensor 22, the regional oximetry sensor 34 may include at least one emitter 38 and at least two detectors 40 and may configured to generate an oxygen saturation signal indicative of blood oxygen saturation within the venous, arterial, and capillary systems within a region of the patient. The patient monitor 30 may include a processor configured to execute code (e.g., stored in a memory of the patient monitor 30) to calculate one or more physiological parameters, such as regional oxygen saturation (e.g., cerebral oxygen saturation), based at least in part on the regional oxygen saturation signal acquired by the regional oximetry sensor 34. The patient monitor 30 may also include a display 42 configured to display information regarding the physiological parameters monitored by the regional oximetry sensor 34, information related to the signal obtained by the regional oximetry sensor 34, information about the system 10, and/or alarm indications, for example. Further, the patient monitor 34 may include various input components 44, such as knobs, switches, keys and keypads, buttons, a touchscreen, etc., to provide for operation and configuration of the patient monitor 30.

Additionally, the EEG monitor 12 may include a display 46 configured to display information regarding the physiological parameters monitored by the EEG sensor 14, by the regional oximetry sensor 22, and/or by the regional oximetry sensor 34, information related to the EEG signals and/or the regional oxygen saturation signals, information about the system 10, and/or alarm indications. For example, the display 46 may display a DOCx 48 for the patient. In some embodiments, the display 34 may display a DOCx for one or more regions of the patient's head (e.g., for each hemisphere of the patient's head). The DOCx 48 may represent a dimensionless number (e.g., ranging from 0, i.e., absence of cerebral activity, to 100, i.e., fully awake and alert) output from a multivariate discriminant analysis that quantifies the overall bispectral properties (e.g., frequency, power, and phase) of the EEG signal. For example, a DOCx 48 between 40 and 60 may indicate an appropriate level for general anesthesia, which may reduce or minimize the occurrence of anesthesia awareness and recall. However, it should be appreciated that the thresholds associated with the various cerebral states (e.g., absence of cerebral activity, under general anesthesia, fully awake and alert, etc.) may vary based on the type of DOCx, such as an EEG index, a BIS™ index, a Narcotrend index, an AAI index, a Sedline™ patient state index (PSI™), an index of consciousness (IoC), a cerebral state index (CSI), and so forth.

The display 46 may also display a regional oxygen saturation value 50 (e.g., a cerebral oxygen saturation value), an EEG waveform 52 based on the EEG signals from the EEG sensor 14, a regional oxygen saturation waveform 54 based on the regional oxygen saturation signals from the regional oximetry sensor 22 and/or the regional oximetry sensor 34. Further, as will be described in more detail below, the display 46 may display a metric 56 (e.g., a confidence level) that is based at least in part on the DOCx and the regional oxygen saturation value. Additionally, the display 46 may display trends 58 over a certain time period (e.g., one hour) for the DOCx, the regional oxygen saturation value, the metric 56, and/or other parameters. Additionally, the EEG monitor 12 may include various control inputs 60, such as knobs, switches, keys and keypads, buttons, a touchscreen, etc., to provide for operation and configuration of the EEG monitor 12. The EEG monitor 12 may also include a speaker to provide information (e.g., alarms) related to the physiological parameters and/or information about the system 10.

Figure 3:
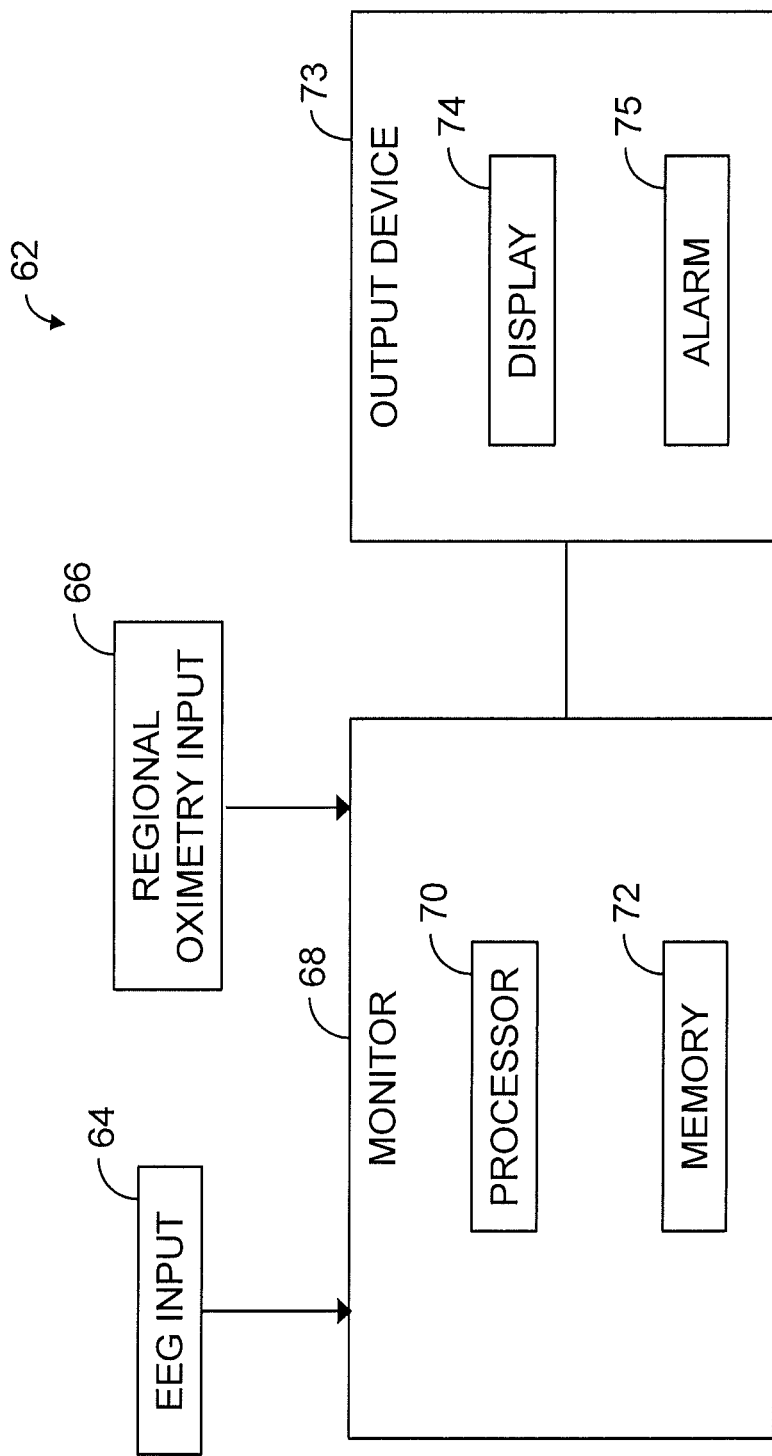
FIG. 3 is a block diagram of a patient monitoring system for monitoring cerebral activity of a patient that includes an EEG input and a regional oximetry input, in accordance with an embodiment.

FIG. 3 is a block diagram illustrating a system 62 for monitoring cerebral activity of a patient. The block diagram illustrates the interactions among some of the components of the system 62, including an EEG input 64, a regional oximetry input 66, and a monitor 68. The monitor 68 includes a processor 70 (e.g., processing circuitry) and a memory 72. The monitor 68 may be the EEG monitor 12, the patient monitor 30, or any other processor-based device. The memory 72 may include instructions, code, and/or algorithms that may be read and executed by the processor 70 to perform the techniques disclosed herein. The system 62 may also include an output device 73. In some embodiments, the processor 70 may be configured to provide signals related to the cerebral activity of the patient, parameters received and/or determined by the processor 70, and/or results, analysis, or determinations determined by the processor 70 to the output device 73. The output device 73 may include any device configured to receive signals from the processor 70 and to visually and/or audibly output information indicative of the information from the signals. For example, the output device 73 may include a display 74 and/or a speaker 75. In some embodiments, the monitor 68 may include the output device 73 (e.g., may be supported by the same housing). In other embodiments, the output device 73 may be separate from the monitor 68. The output device 73 may be any suitable device for conveying information from the signals received from the processor 70, including a computer workstation, a server, a desktop, a notebook, a laptop, a handheld computer, a mobile device, or the like.

In certain embodiments, the EEG input 64 may include an incoming raw or processed (e.g., filtered and/or amplified) EEG signal. In other embodiments, the EEG input 64 may include measured or calculated physiologic data, such as a DOCx. The EEG input 64 may be received from a sensor coupled to the patient (e.g., the EEG sensor 14) or from other medical devices (e.g., the EEG monitor 12). Similarly, the regional oximetry input 66 may include an incoming raw or processed (e.g., filtered and/or amplified) regional oxygen saturation signal, or may include measured or calculated physiological data, such as a regional oxygen saturation value. The regional oximetry input 66 may be received from a sensor coupled to the patient (e.g., the regional oximetry sensor 22 or the regional oximetry sensor 34) or from other medical devices (e.g., the patient monitor 30). In embodiments in which the EEG input 64 and the regional oximetry input 66 include raw or processed signals, the processor 70 may be configured to calculate a DOCx and a regional oxygen saturation value based on the EEG input 64 and the regional oximetry input 66, respectively.

In certain embodiments, the processor 70 may be configured to evaluate or qualify the DOCx based at least in part on the regional oximetry input 66 (e.g., calculated regional oxygen saturation values). For example, the processor 70 may evaluate or qualify the DOCx based on an analysis of regional oxygen saturation values and DOCx values over a period of time. As will be described in more detail below with respect to FIG. 4, the processor 70 may be configured to evaluate the DOCx based on an analysis of a change in the DOCx over a predetermined period and a change in the regional oxygen saturation value over the predetermined period, an analysis of a rate of change in the DOCx over a predetermined period and a rate of change in the regional oxygen saturation over the predetermined period, an analysis of a trend of the DOCx over a predetermined period and a trend in the regional oxygen saturation value over the predetermined period, an analysis of a correlation between the DOCx and the regional oxygen saturation value over a predetermined period, or a combination thereof.

In some embodiments, the processor 70 may evaluate the DOCx by determining a metric (e.g., a numerical value) for the DOCx based on the analysis. The metric may be indicative of the relationship between the DOCx and regional oxygen saturation. For example, the metric may indicate whether the relationship between the DOCx and regional oxygen saturation is expected (e.g., normal) or unexpected (e.g., abnormal, impaired), which may provide useful information to a caregiver for monitoring the cerebral activity of a patient. For example, if the metric indicates that the DOCx and regional oxygen saturation are conforming to an expected relationship, the caregiver may determine that the patient is not experiencing any clinically adverse events, the amount of anesthetic agent delivered to the patient is appropriate, and so forth. If the metric indicates that the DOCx and regional oxygen saturation are not conforming to an expected relationship, this may alert the caregiver to assess the patient (e.g., for clinically adverse events) and/or to assess the amount of anesthetic agent delivered to the patient. In some embodiments, the metric may be a confidence level that is indicative of an estimated level of accuracy, reliability, and/or confidence in the DOCx.

In some embodiments, the processor 70 may determine the value of the metric from a plurality of values. For example, the metric (e.g., confidence level) may be determined from a range of 0 to 1 (e.g., 0, 0.1, 0.2, 0.3, 0.4, 0.5, 0.6, 0.7, 0.8, 0.8, and 1), a range of 1 to 5 (e.g., 1, 2, 3, 4, and 5), a range of 1 to 10, or any other suitable range. In some embodiments, the processor 70 may determine a value of a metric indicative of the relationship between DOCx and regional oxygen saturation from a plurality of values, where each value is associated with a degree or level of expectedness of the relationship. For example, lower values of the metric may indicate a more unexpected relationship and higher values of the metric may indicate a more expected relationship. In some embodiments, the processor 70 may determine a confidence level from a plurality of confidence levels, where each confidence level is indicative of a different level of accuracy, reliability, and/or confidence in the DOCx. For example, lower confidence levels may indicate lower levels of confidence and higher confidence levels may indicate higher levels of confidence. In one embodiment, the metric may be binary (e.g., high confidence or low confidence, expected relationship or unexpected relationship).

The metric may be determined using any suitable techniques. In some embodiments, the processor 70 may determine the metric using one or more algorithms that are a function of the DOCx and regional oxygen saturation, neural networks (e.g., multilayer perception networks (MLP) or radial basis networks), stochastic or probabilistic classifiers (e.g., Bayesian, Hidden Markov Model (HMM), or fuzzy logic classifiers), propositional or predicate logics (e.g., non-monotonic or modal logics), nearest neighbor classification methods (e.g., $k^{th}$ nearest neighbor or learning vector quantization (LVQ) methods), or any other learning-based algorithms. In certain embodiments, the processor 70 may determine the metric using one or more look-up tables and/or one or more databases (e.g., stored in the memory 72). In some embodiments, the processor 70 may determine the metric using one or more profiles (e.g., stored in the memory 72) that are indicative of a relationship between DOCx and regional oxygen saturation, where each profile is associated with a confidence level and/or a degree of expectedness. For example, the one or more profiles may include plots of DOCx values and regional oxygen saturation values over time. The processor 70 may be configured to compare the DOCx values and the regional oxygen saturation values to the plots of the one or more profiles to select a profile, and the processor 70 may use the metric associated with the selected profile.

Figure 4:
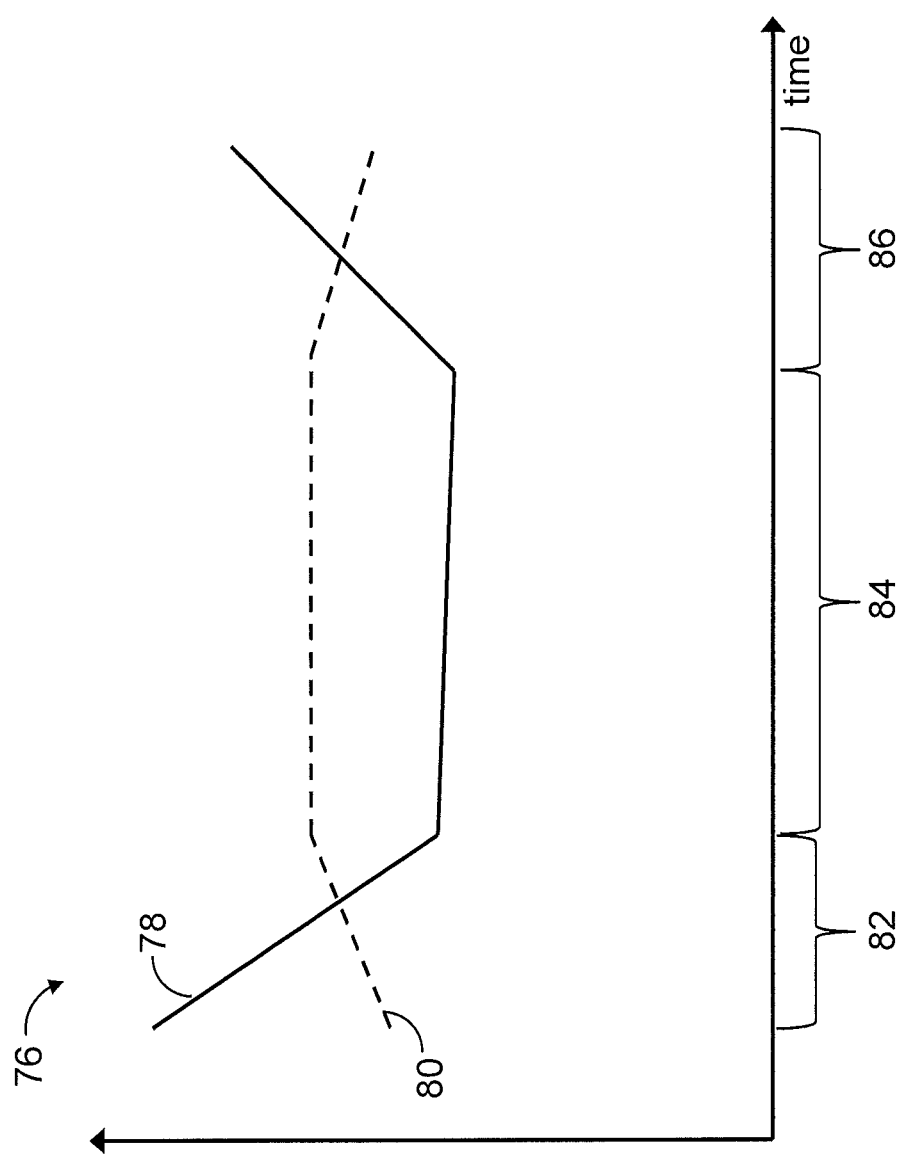
FIG. 4 is a plot of a patient's depth of consciousness index (DOCx) and regional oxygen saturation over time, in accordance with an embodiment.

FIG. 4 illustrates an embodiment of a plot 76 of DOCx values 78 and regional oxygen saturation values 80 over time. As illustrated, the DOCx values 78 generally decrease during a first period 82, remain stable (e.g., within a desired range) during a second period 84, and increase during a third period 86. For example, the first period 82 may be associated with an induction stage of general anesthesia in which anesthetic agents are administered to sedate a patient, the second period 84 may be associated with a maintenance stage of the general anesthesia in which anesthetic agents administered to keep the patient sedated, and the third period 86 may be associated with an emergence period in which the patient is brought out of anesthesia. Further, as illustrated, the decrease in DOCx values 78 is associated with an increase in the regional oxygen saturation values 80, and the increase in the DOCx values 78 is associated with a decrease in the regional oxygen saturation values 80. Additionally, the regional oxygen saturation values 80 remain generally stable as the DOCx values 78 remain generally stable. As noted above, this relationship between the DOCx values 78 and the regional oxygen saturation values 80 may be expected for a normal (i.e., non-impaired) patient. For example, as noted above, an increase in the DOCx may increase the cerebral metabolic rate, which may cause a decrease in regional oxygen saturation, and a decrease in the DOCx may decrease the cerebral metabolic rate, which may increase in regional oxygen saturation. However, it should be appreciated that the plot 76 illustrates an example of one possible relationship between the DOCx values 78 and the regional oxygen saturation values 80, and the present techniques may be implemented using other plots and/or other values of DOCx and regional oxygen saturation.

The processor 70 may be configured to determine a metric (e.g., a confidence level) based on an analysis the DOCx values 78 and the regional oxygen saturation values 80 over a period of time. In particular, the processor 70 may determine the metric based on an analysis of whether the DOCx values 78 and the regional oxygen saturation values 80 generally conform to an expected relationship during the period of time. Accordingly, in some embodiments, the processor 70 may select a predetermined period in which there is an expected relationship between the DOCx values 78 and the regional oxygen saturation values 80. As noted above, there may be an expected relationship between the DOCx values 78 and the regional oxygen saturation values 80 during each of the first period 82, the second period 84, and the third period 86. Accordingly, in some embodiments, the processor 70 may use the first period 82, the second period 84, and/or the third period 86 as a predetermined period. In certain embodiments, the processor 70 may select one or more predetermined periods within the first period 82, the second period 84, and/or the third period 86.

In certain embodiments, the first period 82, the second period 84, and the third period 86 based on the DOCx values 78. For example, the processor 70 may determine the first period 82, the second period 84, and the third period 86 when the DOCx value 78 reaches a predetermined threshold or threshold range. For example, the processor 70 may determine that the patient is the first period 82 when the DOCx value 78 is between approximately 40 and 100, 50 and 100, 60 and 100, or any other suitable range. In some embodiments, the processor 70 may determine that the patient is in the second period 84 when the DOCx value 78 falls below 60, 55, 50, 45, 40, or any other suitable threshold, or when the DOCx value 78 is between approximately 20 and 60, 30 and 60, 40 and 60, or any other suitable range. Further, in some embodiments, the processor 70 may determine that the patient is in the third period 86 when the DOCx value 78 goes above 40, 45, 50, 55, 60, or any other suitable threshold, or when the DOCx value 78 is between approximately 40 and 100, 50 and 100, 60 and 100, or any other suitable range. Further, the processor 70 may determine the first period 82, the second period 84, and the third period 86 based on one or more threshold or threshold ranges and the trend of the DOCx values 78, such as a generally negative trend during the first period 82, a generally stable trend (e.g., stays within a predetermined range) during the second period 84, and a generally positive trend during the third period 86. In some embodiments, the processor 70 may determine the metric based on an analysis of a change in regional oxygen saturation values 80 over a predetermined period and a change in the DOCx values 78 over the same predetermined period. For example, the processor 70 may be configured to determine the difference (i.e., the $rSO_2$ difference) between the regional oxygen saturation value 80 at the beginning of the predetermined period (i.e., $rSO2_{initial}$) and the regional oxygen saturation at the end of the predetermined period (i.e., $rSO2_{end}$), and to determine the difference (i.e., the DOCx difference) between the DOCx at the beginning of the predetermined period (i.e., $DOC_{initial}$) and the DOCx at the end of the predetermined period (i.e., $DOC_{end}$). As noted above, the predetermined period may be the first period 82, the second period 84, or the third period 86, or may be within (e.g., shorter than) the first period 82, the second period 84, or the third period 86. Further, as described below, the processor 70 may determine a metric based on an analysis of whether the $rSO_2$ difference is expected for the DOCx difference and/or for the predetermined period.

For example, the processor 70 may determine a metric based on an analysis of the DOCx difference and the $rSO_2$ difference for the first period 82. As noted above, the DOCx values 78 may be decreasing during the first period 82 and thus, the DOCx difference may be negative. In some embodiments, the DOCx difference during the first period 82 may be between approximately −70 and −10, −60 and −20, −50 and −30, or any other suitable range. In certain embodiments, the DOCx difference during the first period 82 may be based on the threshold or threshold ranges for the first period 82, which may determine $DOC_{initial}$ and/or $DOC_{end}$. In some embodiments, it may be expected to observe increasing regional oxygen saturation values 80, and thus a positive $rSO_2$ difference, during the first period 82 and/or for a negative DOCx difference (e.g., a negative DOCx difference within the threshold ranges listed above). Accordingly, in one embodiment, the processor 70 may determine a high metric (e.g., a high level of confidence or a high value of expectedness) when the DOCx difference is negative and the $rSO_2$ difference is positive during the first period 82, and the processor 70 may determine a low metric (e.g., (e.g., a low level of confidence or a low value of expectedness) when the DOCx difference is negative and the $rSO_2$ difference is negative during the first period 82.

In some embodiments, the memory 72 may store a plurality of thresholds or threshold ranges for the $rSO_2$ difference, and each threshold or threshold range may be associated with a value of the metric and associated with a predetermined period (e.g., the first period 82) and/or a DOCx difference. Accordingly, the processor 70 may be configured to compare the $rSO_2$ difference to one or more thresholds or threshold ranges that are associated with the first period 82 and/or the DOCx difference for the first period 82 to determine the metric. As noted above, the metric may lie within a range of values. While the following discussion refers to a metric range from 0 to 1, where 0 is the least confident (or least expected) and 1 is the most confident (or most expected), it should be noted that any suitable range may be used. In some embodiments, the processor 70 may determine a first level of the metric (e.g., between 0.8 and 1) when the $rSO_2$ difference is within a first threshold range (e.g., between approximately 1 and 10) and a second level of the metric (e.g., between 0.5 and 0.7) when the $rSO_2$ difference is within a second threshold range (e.g., between approximately 11 and 20). Further, in certain embodiments, the processor 70 may determine a third level of the metric (e.g., between 0.2 and 0.4) when the $rSO_2$ difference is within a third threshold range (e.g., between approximately 20 and 40), a fourth level of the metric (e.g., between 0 and 0.1) when the $rSO_2$ difference is within fourth threshold range (e.g., between approximately −1 and −40).

Further, the processor 70 may determine a metric based on an analysis of the DOCx difference and the $rSO_2$ difference for the second period 84. In some embodiments, the second period 84 may include relatively stable DOCx values 78 and thus, the second period 84 may have a relatively low DOCx difference. For example, in some embodiments, the DOCx difference during the second period 84 may be between approximately −20 and 20, −10 and 10, −5 and 5, or any other suitable range. In certain embodiments, the DOCx difference during the second period 84 may be based on the threshold or threshold ranges for the second period 84, which may determine $DOC_{initial}$ and/or $DOC_{end}$. Additionally, it may be expected to observe relatively stable regional oxygen saturation values 80, and thus a relatively low $rSO_2$ difference, during the second period 82 and/or for relatively low DOCx differences (e.g., a DOCx difference within the threshold ranges listed above). Further, the processor 70 may be configured to compare the $rSO_2$ difference to one or more thresholds or threshold ranges that are associated with the second period 84 and/or the DOCx difference for the second period 84 to determine the metric. For example, in some embodiments, the processor 70 may determine a first level of the metric (e.g., between 0.8 and 1) when the $rSO_2$ difference is within a first threshold range (e.g., between approximately −5 and 5), a second level of the metric (e.g., between 0.5 and 0.7) when the $rSO_2$ difference is within a second threshold range (e.g., between approximately −10 and −6 or between approximately 6 and 10), and so forth.

Additionally, the processor 70 may determine a metric based on an analysis of the DOCx difference and the $rSO_2$ difference for the third period 86. As noted above, the DOCx values 78 may be increasing during the third period 86 and thus, the DOCx difference may be positive. In some embodiments, the DOCx difference during the third period 86 may be between approximately 10 and 70, 20 and 60, 30 and 50, or any other suitable range. In certain embodiments, the DOCx difference during the third period 86 may be based on the threshold or threshold ranges for the third period 86, which may determine $DOC_{initial}$ and/or $DOC_{end}$. In some embodiments, it may be expected to observe decreasing regional oxygen saturation values 80, and thus a negative $rSO_2$ difference, during the third period 86 and/or for a positive DOCx difference (e.g., a positive DOCx difference within the threshold ranges listed above). Accordingly, in one embodiment, the processor 70 may determine a high level of the metric when the DOCx difference is positive and the $rSO_2$ difference is negative during the third period 86, and the processor 70 may determine a low level of the metric when the DOCx difference is positive and the $rSO_2$ difference is positive during the third period 86.

Further, the processor 70 may be configured to compare the $rSO_2$ difference to one or more thresholds or threshold ranges that are associated with the third period 86 and/or the DOCx difference for the third period 86 to determine the metric. For example, the processor 70 may determine a first metric (e.g., between 0.8 and 1) when the $rSO_2$ difference is within a first threshold range (e.g., between approximately −1 and −10) and a second metric (e.g., between 0.5 and 0.7) when the $rSO_2$ difference is within a second threshold range (e.g., between approximately −11 and −20). Further, in certain embodiments, the processor 70 may determine a third metric (e.g., between 0.2 and 0.4) when the $rSO_2$ difference is within a third threshold range (e.g., between approximately −20 and −40), a fourth metric (e.g., between 0 and 0.1) when the $rSO_2$ difference is within fourth threshold range (e.g., between approximately 1 and 40).

Additionally, in some embodiments, the processor 70 may determine the metric using a function of the fractional changes of DOCx and regional oxygen saturation, where the fractional change of DOCx is defined by the ratio of the DOCx difference with respect to $DOC_{initial}$ and the fractional change of regional oxygen saturation is defined by the ratio of the $rSO_2$ difference with respect to $rSO2_{initial}$. For example, the memory 72 may store a look-up table or database including a plurality of combinations of fractional changes of the DOCx and regional oxygen saturation, wherein each combination is associated with a value of the metric. Accordingly, the processor 70 may use the determined fractional change in DOCx and the determined fractional change in regional oxygen saturation in the look-up table to determine the metric.

In some embodiments, the processor 70 may be configured to evaluate the determine the metric based at least in part on a trend of the regional oxygen saturation values 80 over a predetermined period and a trend of DOCx values 78 over the same predetermined period. For example, the processor 70 may be configured to use regression analysis, such as linear regression, ordinary least squares regression, nonlinear regression, general linear model regression, and the like, to analyze the trends (e.g., to determine the slopes) of the regional oxygen saturation values 80 and the DOCx values 78. As noted above, it may be desirable to use the first period 82, the second period 84, and/or the third period 86 (or one or more portions of the first period 82, the second period 86, and/or the third period 86) as the predetermined period, because there may be an expected relationship between the trend of the DOCx values 78 and the trend of the regional oxygen saturation values 80 during the first period 82, the second period 84, and the third period 86. For example, in some embodiments, the processor 70 may determine a high metric if the DOCx trend is negative and the regional oxygen saturation trend is positive (e.g., during the first period 82), and the processor 70 may determine a high metric if the DOCx trend is positive and the regional oxygen saturation trend is negative (e.g., during the third period 86). Further, the processor 70 may determine a low metric if a regression line for the DOCx trend has a relatively flat slope (e.g., the slope is within a predetermined range) and a regression line for the regional oxygen saturation trend has a slope that is greater than a positive threshold or is less than a negative threshold (e.g., during the second period 84). Alternatively, the processor 70 may determine a high metric if the regression lines for both the DOCx trend and the regional oxygen saturation trend have relatively flat slopes (e.g., during the second period 84). In certain embodiments, the processor 70 may determine a low metric if both trends are positive or if both trends are negative.

Further, in some embodiments, the processor 70 may compare the trend of the DOCx values 78 and the trend of the regional oxygen saturation values 80 to one or more profiles to determine the metric. For example, the memory 72 may store a plurality of profiles, where each profile includes a DOCx trend and a regional oxygen saturation trend and is associated with a level of the metric. The processor 70 may be configured to compare the DOCx values 78 and the regional oxygen saturation values 80 to select a profile (e.g., a profile that includes a DOCx trend and a regional oxygen saturation trend that best matches the DOCx values 78 and the regional oxygen saturation values 80), and the processor 70 may use the level of the metric associated with the selected profile.

In certain embodiments, the memory 72 may store a look-up table or database that includes a plurality of combinations of slopes (or ranges of slopes) for the DOCx trend and the regional oxygen saturation trend, where each combination of slopes is associated a level of the metric. For example, the look-up table may include a first metric that is associated with a first DOCx slope (or a first range in DOCx slopes) and a first regional oxygen saturation slope (or a first range in regional oxygen saturation slopes), a second metric that is associated with a second DOCx slope (or a second range in DOCx slopes) and a second regional oxygen saturation slope (or a second range in regional oxygen saturation slopes), and so forth. Accordingly, the processor 70 may use the slopes of the DOCx values 78 and the regional oxygen saturation values 80 with the look-up table to determine the metric.

Additionally, in some embodiments, the processor 70 may determine the metric based at least in part on a correlation between the DOCx and the regional oxygen saturation value over a predetermined period. For example, the processor 70 may be configured to determine the linear correlation between the DOCx values 78 and the regional oxygen saturation values 80 using a linear regression line (e.g., a best-fit line). In some embodiments, the processor 70 may determine a Pearson coefficient (e.g., Pearson correlation coefficient) to determine the linear correlation between the DOCx values 78 and the regional oxygen saturation values 80. The Pearson coefficient may be between −1 and 1, where −1 represents total negative correlation, 1 represents total positive correlation, and 0 represents the absence of correlation. In certain embodiments, the processor 70 may determine the metric based at least in part on the Pearson coefficient. For example, the memory 72 may store a look-up table or database that includes a plurality of values of the Pearson coefficient (e.g., any value within the range of −1 and 1), where each value is associated with a level of the metric (e.g., a confidence level). The processor 70 may access the look-up table or database using the value of the Pearson coefficient to determine the level of the metric.

In some embodiments, the processor 70 may determine the metric based on the Pearson coefficient and the predetermined period (e.g., the first period 82, the second period 84, or the third period 86) and/or stages of general anesthesia, such as an anesthesia induction stage when anesthetic agents are provided to the patient to reduce the patient's depth of consciousness, an anesthesia maintenance stage when anesthetic agents are provided to the patient to maintain the patient's depth of consciousness within a desired range (e.g., sedated during a surgical procedure), and/or an anesthesia emergence stage when delivery of anesthetic agents to the patient is reduced and/or stopped to increase the patient's depth of consciousness. For example, the memory 72 may store a look-up table or database that includes a plurality of combinations of values of the Pearson coefficient and stages of general anesthesia, where each combination of a value of the Pearson coefficient and a stage of general anesthesia (e.g., anesthesia induction, anesthesia maintenance, or anesthesia emergence) is associated with a level of the metric. For example, a negative Pearson coefficient may be expected during the first period 82, the third period 86, anesthesia induction, and/or anesthesia emergence and may indicate high levels of confidence in the DOCx. In some embodiments, little or no correlation (e.g., a low or near 0 Pearson coefficient) may be expected during the second period 84 and/or during anesthesia maintenance. In some embodiments, during the first period 82, the third period 86, anesthesia induction, and/or anesthesia emergence, the processor 70 may determine a first metric (e.g., between 0.8 and 1) when the Pearson coefficient is between −1 and −0.5, a second metric (e.g., between 0.5 and 0.7) when the Pearson coefficient is between −0.4 and −0.2, a third metric (e.g., between 0.2 and 0.4) when the Pearson coefficient is between −0.1 and 0.1, and a fourth metric (e.g., between 0 and 0.1) when the Pearson coefficient is between 0.2 and 1. In certain embodiments, during the second period 84 and/or anesthesia maintenance, the processor 70 may determine a first metric (e.g., between 0.8 and 1) when the Pearson coefficient is between −0.2 and 0.2, a second metric (e.g., between 0.5 and 0.7) when the Pearson coefficient is between −0.4 and −0.3 or between 0.3 and 0.4, and a third metric (e.g., between 0 and 0.4) when the Pearson coefficient is between −1 and −0.5 or between 0.5 and 1.

In some embodiments, the processor 70 may determine the stage of general anesthesia (e.g., anesthesia induction, anesthesia maintenance, or anesthesia emergence) for the predetermined period (e.g., determine which stage of anesthesia the predetermined period falls within or occurs during). In some embodiments, the processor 70 may determine the stage of general anesthesia based on values and/or trends of the depth of consciousness index alone or in combination with values and/or trends of other physiological parameters (e.g., blood pressure, heart rate, respiration rate, regional oxygen saturation, etc.). Additionally or alternatively, the processor 70 may determine the stage of general anesthesia based on inputs from medical monitors, inputs from medical devices (e.g., injection devices configured to deliver anesthetic agents to the patient, titration devices configured to measure amounts or rates of anesthetic agents delivered to the patient, etc.), and/or user inputs (e.g., indicating the stage).

Further, in certain embodiments, the metric may be calculated based at least in part on a ratio of the DOCx with respect to the regional oxygen saturation value (i.e., by dividing the DOCx by the regional oxygen saturation value). In one embodiment, the metric may be based on the product of the ratio and a coefficient, which may be empirically determined and stored in the memory 72. In some embodiments, the metric may be determined by analyzing the ratio over a predetermined period of time (e.g., the first period 82, the second period 84, and/or the third period 86). For example, the ratio may be expected to decrease during the first period 82, remain relatively stable during the second period 84, and increase during the third period 86.

The processor 70 may be configured to provide a signal indicative of the metric and/or the determined accuracy, reliability, and/or confidence level of the DOCx to the output device 73. For example, in some embodiments, the processor 70 may cause the display 74 to display the DOCx, the metric, and/or a visual indication of the metric (e.g., the expectedness or the accuracy and/or reliability of the DOCx). In one embodiment, the processor 70 may cease or prevent display of the DOCx if the processor 70 determines that the DOCx is likely unreliable and inaccurate based on the confidence level. For example, for a range of confidence levels from 0 to 1, the processor 70 may determine that the DOCx is highly unreliable and/or inaccurate when the confidence level is between 0 and 0.3, likely unreliable and/or inaccurate when the confidence level is between 0.4 and 0.5, likely reliable and/or accurate when the confidence level is between 0.6 and 0.7, and highly reliable and/or accurate when the confidence level is between 0.8 and 1. Further, the processor 70 may provide a signal (e.g., an alarm signal) indicative of a low confidence level or low expectedness level to the output device 73 if the metric is less than a metric threshold (e.g., 0.5. 0.4, 0.3, 0.2, 0.1, or 0 on a 0 to 1 scale). The signal may cause the speaker 75 to provide an alarm and/or cause the display 74 to display an alarm indication (e.g., a textual message, a graphical indicator, etc.).

Further, in certain embodiments, the processor 70 may use the metric (e.g., the confidence level) as a signal quality measure within the algorithm for calculating DOCx. For example, in some embodiments, the processor 70 may calculate DOCx (e.g., a current, displayed, and/or outputted value of DOCx) based on one or more historical values of DOCx (e.g., previously calculated values of DOCx). For example, the processor 70 may calculate DOCx based on EEG data at a time point (e.g., a current time point) and based on one or more historical values of the DOCx at one or more previous time points (e.g., before the current time point). For example, the processor 70 may calculate DOCx using a weighted average of the current DOCx and one or more historical values of the DOCx. In some embodiments, the processor 70 may discard one or more historical values of DOCx for the calculation DOCx (e.g., may not use one or more historical values of DOCx in the algorithm for calculating DOCx) if the metric for the one or more historical values of DOCx is below a threshold. In certain embodiments, the processor 70 may decrease a weight of one or more historical values of DOCx for the calculation DOCx (e.g., may decrease a contribution of one or more historical values of DOCx in the algorithm for calculating DOCx) if the metric for the one or more historical values of DOCx is below a threshold. Thus, the processor 70 may use the metric as a signal quality measure to discard or reduce a contribution of a historical value of DOCx if the metric indicates that the historical value of DOCx is likely inaccurate or unreliable, which may increase the accuracy and reliability of the calculated DOCx (e.g., a current value of DOCx).

The present embodiments also provide various methods for monitoring the cerebral activity of a patient based at least in part on EEG signals of the patient and regional oximetry signals of the patient. The methods disclosed herein include various steps represented by blocks. It should be noted any of the methods provided herein, may be performed as an automated procedure by a system, such as system 10, or by a processor-based device, such as the EEG monitor 12, the patient monitor 30, and/or the monitor 68. Although the flow charts illustrate the steps in a certain sequence, it should be understood that the steps may be performed in any suitable order and certain steps may be carried out simultaneously, where appropriate. Further, certain steps or portions of the methods may be performed by separate devices.

Figure 5:
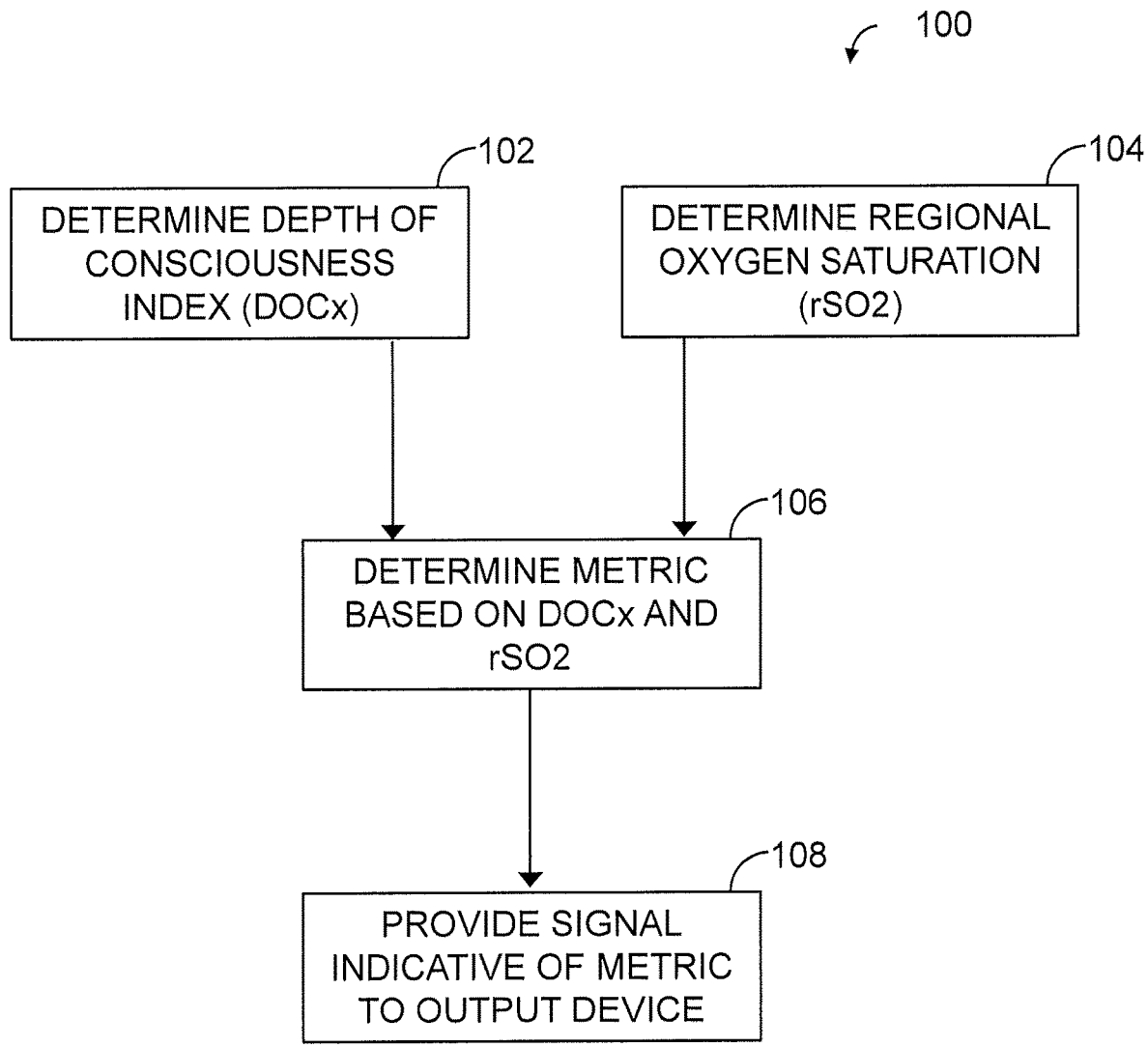
FIG. 5 is flow diagram of a method for monitoring a patient's cerebral activity based at least in part on a depth of consciousness index (DOCx) and a regional oximetry saturation value, in accordance with an embodiment.

FIG. 5 illustrates a method for monitoring the cerebral activity of a patient. The method 100 may include determining a DOCx for a patient (block 102). For example, the processor 70 may determine the DOCx based on the EEG input 64, which may be received from the EEG sensor 14 or the EEG monitor 14. Additionally, the method 100 may include determining a regional oxygen saturation value for the patient (block 104). For example, the processor 70 may determine the regional oxygen saturation value based on the regional oximetry input 66, which may be received from the regional oximetry sensor 22, the regional oximetry sensor 34, or the patient monitor 30. It should be appreciated that, in some embodiments, the determining steps 102 and 104 may be performed continuously or at predetermined intervals over a period of time.

The method 100 may also include determining a metric (e.g., a value, an index, etc.) associated with the patient's cerebral activity based at least in part on the DOCx and the regional oxygen saturation value (block 106). The metric may be a numerical value. The metric may be indicative of a relationship between the DOCx and regional oxygen saturation. In particular, the metric may indicate whether the relationship between the DOCx and regional oxygen saturation is expected (e.g., normal) or unexpected (e.g., abnormal, impaired). In certain embodiments, the metric may be a confidence level for the DOCx indicative of the accuracy, reliability, and/or confidence in the DOCx, as described above in FIGS. 3 and 4. In some embodiments, the metric may be indicative of a relationship between the DOCx and the regional oxygen saturation value. Additionally, the method 100 may include providing a signal indicative of the metric to an output device (block 108). For example, the processor 70 may provide the metric to the output device 73, which may cause the output device 73 to display the metric on the display 74 and/or to provide audible indications (e.g., alarms) for the metric. Further, the processor 70 may provide the DOCx and/or the regional oxygen saturation value to the output device 73 for display and/or audible indications.

Figure 6:
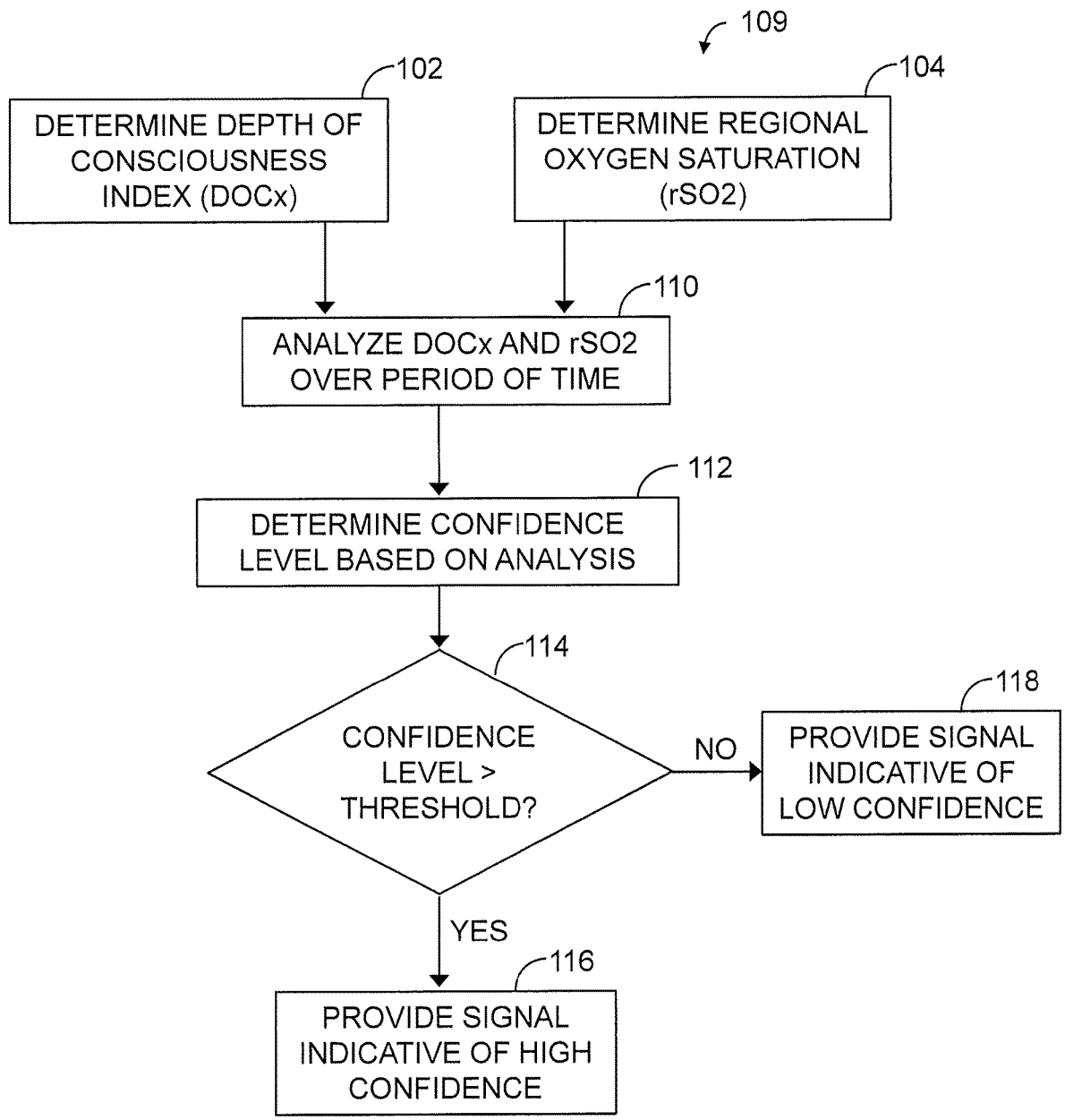
FIG. 6 is flow diagram of a method for evaluating a depth of consciousness index (DOCx) based at least in part on regional oximetry data, in accordance with an embodiment.

FIG. 6 illustrates a method 109 for evaluating a DOCx of a patient based least in part on regional oximetry data of the patient. The method 109 may include determining a DOCx for a patient (block 102) and determining a regional oxygen saturation value for the patient (block 104), as described above in FIG. 5. The method 109 may also include analyzing the DOCx and the regional oxygen saturation value over a predetermined period (block 110). For example, as described in detail above in FIGS. 3 and 4, the processor 70 may be configured to analyze a change in the DOCx over the predetermined period and a change in the regional oxygen saturation value over the predetermined period, a trend of the DOCx over a predetermined period and a trend in the regional oxygen saturation value over the predetermined period, a correlation between the DOCx and the regional oxygen saturation value over a predetermined period, any other suitable information relating to the DOCx and/or the regional oxygen saturation value over a predetermined period, or a combination thereof. Additionally, the method may include determining a confidence level for the DOCx based on the analysis (block 112). For example, as described in detail above in FIGS. 3 and 4, the processor 70 may be configured to determine a confidence level indicative of the accuracy and reliability of the DOCx based on the analysis.

The method 109 may further include determining whether the confidence level is greater than a confidence threshold (query 114). For example, the processor 70 may compare the determined confidence level to a confidence threshold stored in the memory 72 or a confidence threshold inputted by a user (e.g., using the control inputs 44 and/or 60). In some embodiments, the confidence threshold may be 0.5, 0.4, 0.3, 0.2, 0.1, or 0 on a scale of confidence levels between 0 and 1, where 0 is the lowest confidence level and 1 is the highest confidence level. If the confidence level is greater than the confidence threshold, the method 109 may include providing a signal (e.g., an alarm signal) indicative of high confidence for the DOCx to an output device (block 116). For example, as noted above, the processor 70 may cause the display 74 to display the DOCx and the confidence level and/or an indication of the confidence level. If the confidence level is less than the confidence threshold, the method 109 may include providing a signal (e.g., an alarm signal) indicative of low confidence for the DOCx to an output device (block 118). For example, the processor 70 may cause the display 74 to display the DOCx and the confidence level and/or an indication of the confidence level. Additionally or alternatively, the processor 70 may cause the speaker 75 to activate an alarm if the confidence level is less than the confidence threshold. In some embodiments, the processor 70 may not compare the confidence level to a confidence threshold, and the processor 70 may cause display of the confidence level or may provide any suitable indication of the confidence level.

As described in detail above, a metric (e.g., a confidence level) may be determined based at least in part on the DOCx and the regional oxygen saturation of the patient. However, as noted above, deviations in the regional oxygen saturation not associated with metabolic demand may occur if the patient is impaired, for example, due to a traumatic brain injury, an ischemic event, a stroke, or a seizure. As such, the confidence level that is determined based on the patient's regional oxygen saturation and the DOCx may not be as accurate or reliable while the patient is impaired. Accordingly, FIGS. 7 and 8 relate to techniques for monitoring a patient's cerebral activity based at least in part on the DOCx, the regional oxygen saturation, and the cerebral autoregulation information of the patient. In particular, the cerebral autoregulation information may be used to evaluate, qualify, and/or adjust the metric (e.g., the confidence level) determined based on the DOCx and regional oxygen saturation.

Figure 7:
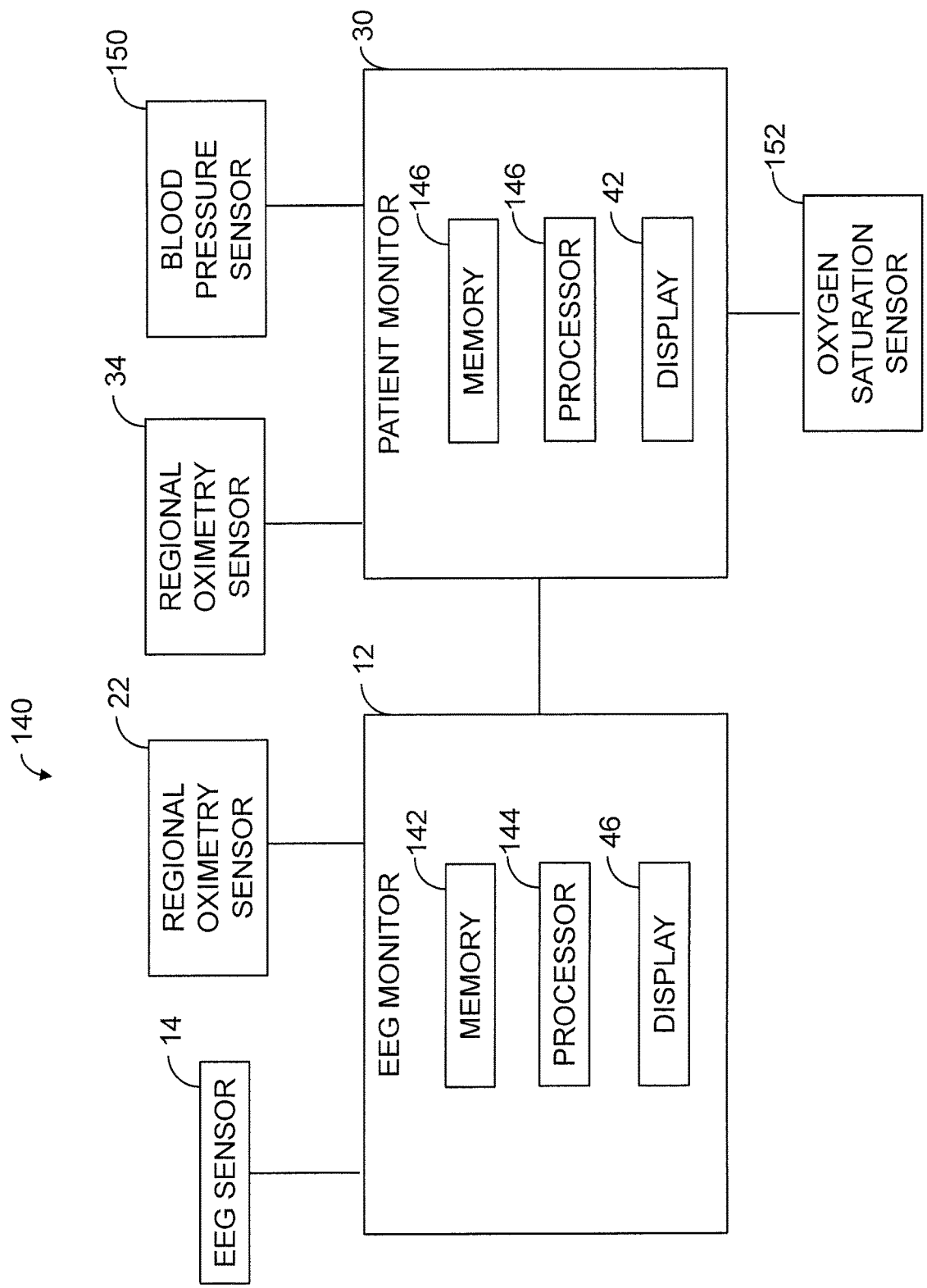
FIG. 7 is a block diagram of a patient monitoring system for monitoring cerebral activity of a patient based on cerebral autoregulation information, in accordance with an embodiment.

With the foregoing in mind, FIG. 7 illustrates an embodiment of a patient monitoring system 140 for monitoring the cerebral activity of a patient based at least in part on cerebral autoregulation information of the patient. As illustrated, the system 140 may include the EEG monitor 12 and the EEG sensor 14, as described above with respect to FIG. 2, to determine the DOCx of the patient. The EEG monitor 12 may include a memory 142 configured to store instructions and algorithms and a processor 144 configured to execute the instructions and algorithms to implement the techniques disclosed herein. The EEG monitor 12 may be communicatively coupled to the regional oximetry sensor 22 and/or the patient monitor 30, and the EEG monitor 12 may receive a raw or processed regional oxygen saturation signal or a calculated regional oxygen saturation value from the regional oximetry sensor 22 and/or the patient monitor 30. Additionally, the patient monitor 30 may include a memory 146 configured to store instructions and algorithms and a processor 148 configured to execute the instructions and algorithms to implement the techniques disclosed herein. In some embodiments, the patient monitor 30 and the EEG monitor 12 may be one integrated monitor.

The system 140 may also include a blood pressure sensor 150. The blood pressure sensor 150 may be communicatively coupled to the patient monitor 30, the EEG monitor 12, and/or or any other suitable processor-based device. The blood pressure sensor 150 may be any sensor or device configured to obtain the patient's blood pressure (e.g., arterial blood pressure). For example, the blood pressure sensor 150 may include a blood pressure cuff for non-invasively monitoring blood pressure or an arterial line for invasively monitoring blood pressure. In certain embodiments, the blood pressure sensor 150 may include one or more pulse oximetry sensors. In some such cases, the patient's blood pressure may be derived by processing time delays between two or more characteristic points within a single plethysmography (PPG) signal obtained from a single pulse oximetry sensor. Various techniques for deriving blood pressure based on a comparison of time delays between certain components of a single PPG signal obtained from a single pulse oximetry sensor is described in U.S. Publication No. 2009/0326386, entitled "Systems and Methods for Non-Invasive Blood Pressure Monitoring," the entirety of which is incorporated herein by reference. In other cases, the patient's blood pressure may be continuously, non-invasively monitored via multiple pulse oximetry sensors placed at multiple locations on the patient's body. As described in U.S. Pat. No. 6,599,251, entitled "Continuous Non-invasive Blood Pressure Monitoring Method and Apparatus," the entirety of which is incorporated herein by reference, multiple PPG signals may be obtained from the multiple pulse oximetry sensors, and the PPG signals may be compared against one another to estimate the patient's blood pressure. Regardless of its form, the blood pressure sensor 150 may be configured to generate a blood pressure signal indicative of the patient's blood pressure (e.g., arterial blood pressure) over time and may provide the blood pressure signal to the patient monitor 30 or to any other suitable processing device, such as, for example, EEG monitor 12 or the monitor 68, to enable evaluation of the patient's cerebral autoregulation status.

The patient monitor 30 may be configured to determine a cerebral autoregulation status based at least in part on a relationship between the measured blood pressure from the blood pressure sensor 150 and the measured oxygen saturation (e.g., regional oxygen saturation) from the regional oximetry sensor 34. The patient monitor 30 may determine the cerebral autoregulation status using any suitable techniques, such as the techniques described in U.S. Publication No. 2014/0073888, entitled "Non-Invasive Method for Monitoring Autoregulation," U.S. Publication No. 2014/0073930, entitled "Measure of Brain Vasculature Compliance as a Measure of Autoregulation," and U.S. application Ser. No. 14/881,455, entitled "System and Method for Monitoring Autoregulation," the entireties of which are incorporated by reference herein for all purposes. For example, the patient monitor 30 may determine a cerebral oximetry index (COx) based on the blood pressure signal and the regional oxygen saturation signal. The COx is indicative of vascular reactivity, which is related to cerebral blood vessels' ability to control proper blood flow, via vasoconstriction (a narrowing of the blood vessel) and/or vasodilation (expansion of the blood vessel). Thus, the COx is also indicative of whether the patient's cerebral autoregulation is impaired.

The patient monitor 30 may derive the COx by determining a linear correlation between blood pressure measurements and regional oxygen saturation measurements. The linear correlation may be based on a Pearson coefficient, which may be defined as the covariance of the measured blood pressure (e.g., arterial blood pressure) and oxygen saturation divided by the product of their standard deviations. For example, the patient monitor 30 may assign a value to COx based on the determined Pearson coefficient, which may be between −1 and 1, inclusive, where −1 represents total negative correlation, +1 represents total positive correlation, and 0 represents the absence of correlation between the blood pressure measurements and the oxygen saturation measurements. Thus, COx values between −1 and 0 may suggest that cerebral autoregulation is working properly, while COx values between 0 and 1 may suggest that the cerebral autoregulation is impaired. In some cases, a predetermined threshold between 0 and 1 may be utilized to determine whether the patient's cerebral autoregulation is impaired.

The patient monitor 30 may be configured to determine the patient's cerebral autoregulation status based on the COx value. In some embodiments, the patient monitor 30 may determine a first cerebral autoregulation status indicating that the cerebral autoregulation is functioning properly when the COx is between −1 and 0, and a second cerebral autoregulation status indicating that the cerebral autoregulation is not functioning properly (e.g., impaired) when the COx is between 0 and 1. In some embodiments, the patient monitor 30 may cause display of the COx and/or the cerebral autoregulation status (e.g., on the display 42, the display 46, and/or the display 74).

Further, in some embodiments, the patient monitor 30 may be configured to normalize (e.g., correct) the regional oxygen saturation signal or measurements. In particular, the patient monitor 30 may be configured utilize any of the techniques described in U.S. Provisional Application No. 62/237,871, entitled "System and Method for Monitoring Autoregulation Utilizing Normalized Regional Oxygen Saturation Values," which is hereby incorporated by reference in its entirety for all purposes, to normalize the regional oxygen saturation signal or measurements. For example, the patient monitor 30 may receive an oxygen saturation signal indicative of blood oxygen saturation within the pulsatile tissue of the patient and may use the oxygen saturation signal to normalize the regional oxygen saturation signal or measurements based on a relationship with oxygen saturation (e.g., remove variations in the regional oxygen saturation due to changes in oxygen saturation). The patient monitor 30 may receive the oxygen saturation signal from the blood pressure sensor 150 and/or from an oxygen saturation sensor 152 (e.g., a pulse oximetry sensor). For example, the oxygen saturation sensor 152 may include an emitter (e.g., at least two light emitting diodes) configured to emit at different wavelengths of light (e.g., red and infrared light) and a detector configured to detect light after passing through the pulsatile tissue of the patient. The patient monitor 30 may be configured to use the normalized regional oxygen saturation to determine the COx and the patient's autoregulation status. Further, in some embodiments, the normalized regional oxygen saturation may be used in the evaluation of the DOCx. For example, the monitor 30 may use the normalized regional oxygen saturation to determine the metric or may provide the normalized regional oxygen saturation to another processing device (e.g., the EEG monitor 12, the monitor 86, etc.) for use in determining the metric.

As noted above, if cerebral autoregulation is impaired, there may be deviations in regional oxygen saturation that are not associated with cerebral metabolic rate. As such, the confidence level determined based on DOCx and regional oxygen saturation may not be accurate or reliable when cerebral autoregulation is impaired. Thus, in some embodiments, the patient monitor 30, the EEG monitor 12, and/or the monitor 68 may use the COx value and/or the patient's cerebral autoregulation status to evaluate, qualify, and/or adjust the confidence level determined based on the DOCx and regional oxygen saturation.

Figure 8:
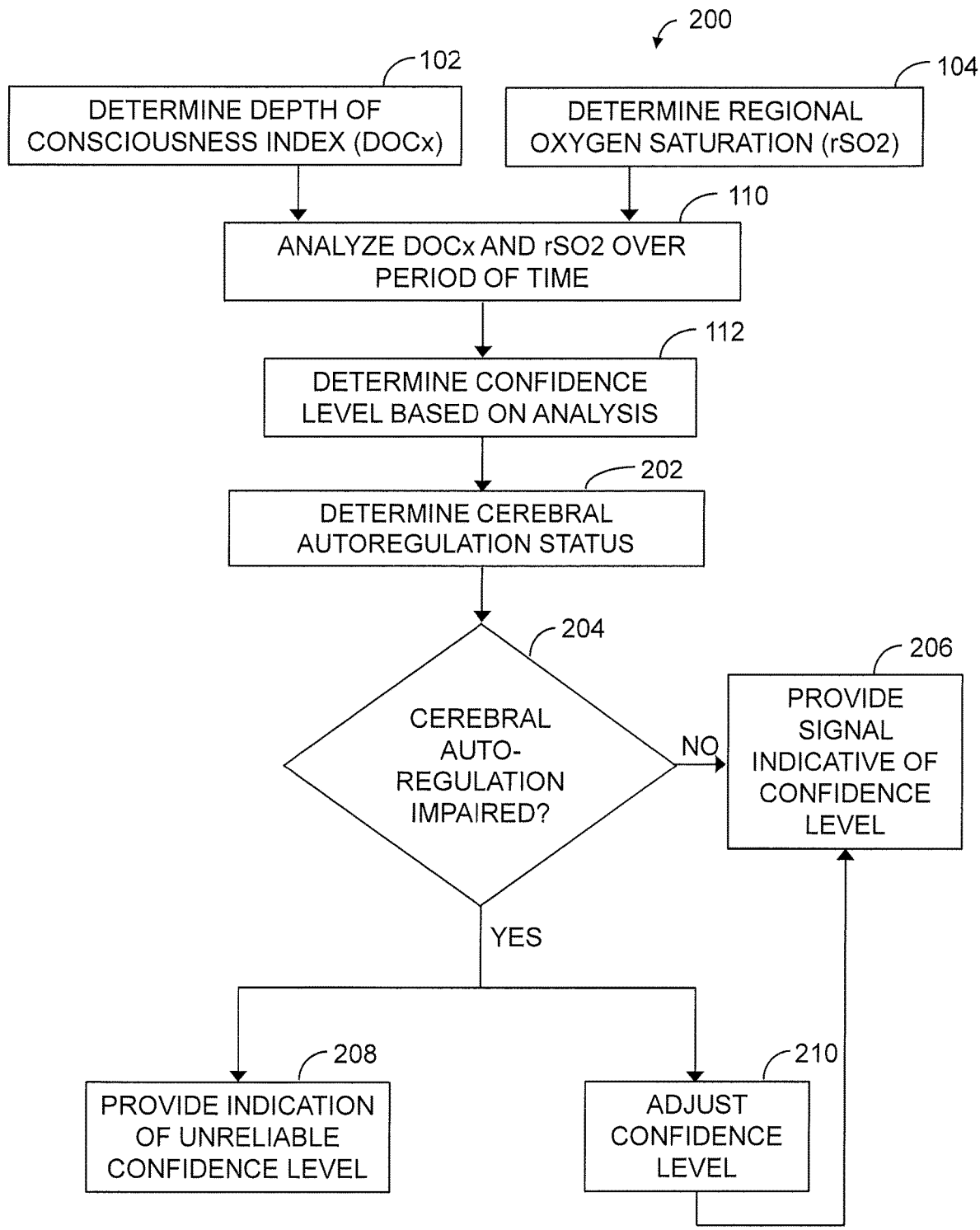
FIG. 8 is a flow diagram of a method for evaluating a DOCx and/or a confidence level of a patient based on cerebral autoregulation information, in accordance with an embodiment.

For example, FIG. 8 illustrates a method 200 for evaluating the DOCx of a patient based at least in part on cerebral autoregulation information of the patient. The method 200 may include determining a DOCx for a patient (block 102) and determining a regional oxygen saturation value for the patient (block 104), as described above in FIG. 5. Additionally, the method 200 may include analyzing the DOCx and the regional oxygen saturation value over a predetermined period (block 110) determining a confidence level for the DOCx based on the analysis (block 112), as described above in FIG. 6. The method 200 may also include determining a cerebral autoregulation status of the patient (block 202). For example, the processor 70 may determine the cerebral autoregulation status (e.g., impaired or functioning properly) based on the regional oxygen saturation signal (which may be normalized or corrected) and the blood pressure signal, as described above. In particular, the processor 70 may determine the COx, which may be used to determine the cerebral autoregulation status. In certain embodiments, the processor 70 may receive the cerebral autoregulation status and/or the COx from another processor-based device (e.g., the patient monitor 30).

Further, the method 200 may include determining whether the cerebral autoregulation is impaired based on the cerebral autoregulation status (query 204). If cerebral autoregulation is functioning properly and is not impaired, the processor 70 may provide a signal indicative of the confidence level to the output device 73 (block 206). For example, the processor 70 may cause display of the confidence level on the display 74. The display of the confidence level may indicate to a caregiver that the confidence level is likely accurate and reliable and may be beneficial to use to evaluate the accuracy and/or reliability of the DOCx. Additionally, the processor 70 may cause display of the cerebral autoregulation status and/or the COx. In some embodiments, the processor 70 may be configured to adjust (e.g., increase) the confidence level and cause display of the adjusting confidence level. For example, the processor 70 may increase the confidence level by a preset amount (e.g., 0.1 or 0.2 on a 0 to 1 scale) when cerebral autoregulation is functioning properly or may increase the confidence level by an amount that is based on the COx (e.g., increase by 0.1 when the COx is between −0.3 and −0.6, increase by 0.2 when the COx is between −0.7 and −1, etc.).

If the cerebral autoregulation is impaired, the processor 70 may provide an indication that the confidence level may be inaccurate or unreliable (block 208). For example, in certain embodiments, the processor 70 may not cause display of the confidence level or may stop display of a displayed confidence level. In some embodiments, the processor 70 may cause display of the confidence level and an indication (e.g., text, a graphic, etc.) that the confidence level may not be accurate and/or reliable. In certain embodiments, the processor 70 may provide an alarm signal to the output device 73 that is indicative of an alarm condition of the confidence level (e.g., the confidence level is inaccurate or unreliable).

In some embodiments, the processor 70 may adjust the confidence level in response to a determination that the cerebral autoregulation is impaired (block 210). For example, the processor 70 may adjust (e.g., increase or decrease) the confidence level by a preset amount (e.g., 0.1 or 0.2 on a 0 to 1 scale) when cerebral autoregulation is impaired. In some embodiments, the processor 70 may adjust (e.g., increase or decrease) the confidence level by an amount that is based on the COx. Greater values of COx (e.g., 0.7 to 1) may indicate a higher degree or more severe impairment of the cerebral autoregulation, which may be indicative of larger deviations in the regional oxygen saturation. For example, the processor 70 may adjust the confidence level by 0.1 when the COx is between 0.3 and 0.6 and by 0.2 when the COx is between 0.7 and 1. In some embodiments, the processor 70 may adjust the confidence level based on the confidence level and the cerebral autoregulation status (e.g., the COx). That is, the deviations in regional oxygen saturation due to impaired cerebral autoregulation may result in an overly high confidence level or an overly low confidence level. For example, if the confidence level is less than a lower threshold (e.g., 0.5, 0.4, or 0.3 on a 0 to 1 scale), the processor 70 may increase the confidence level by a preset amount or an amount that is based on the COx. If the confidence level is greater than an upper threshold (e.g., 0.5, 0.6, or 0.7 on a 0 to 1 scale), the processor 70 may decrease the confidence level by a preset amount or an amount that is based on the COx. Additionally, the method 200 may include providing a signal indicative of the confidence level to the output device 73 (block 206). For example, the processor 70 may cause the display 74 to display the adjusted confidence level.

The processors described above (e.g., the processors 70, 144, and 148) may include multiple microprocessors, one or more special-purpose microprocessors, one or more application specific integrated circuits (ASICS), one or more reduced instruction set (RISC) processors, or some combination thereof. Additionally, the memory devices described above (e.g., the memory devices 72, 142, and 146) may include a volatile memory, such as random access memory (RAM), and/or a nonvolatile memory, such as ROM. The memory devices 72, 142, and 146 may include one or more tangible, non-transitory, machine-readable media collectively storing instructions executable by the processors 70, 144, and/or 148 to perform the methods and control actions described herein. Such machine-readable media can be any available media that can be accessed by the processors 70, 144, and/or 148 or by any general purpose or special purpose computer or other machine with a processor. The memory devices 72, 142, and 146 may store a variety of information and may be used for various purposes. For example, the memory devices 72, 142, and 146 may store processor-executable instructions (e.g., firmware or software) for the processors 70, 144, and/or 148 to execute, such as instructions for carrying out any of the techniques discloses herein. The memory devices 72, 142, and 146 (e.g., nonvolatile storage) may include read-only memory (ROM), flash memory, a hard drive, or any other suitable optical, magnetic, or solid-state storage medium, or a combination thereof. The memory devices 72, 142, and 146 may store data (e.g., the EEG signal, the regional oxygen saturation signal, blood pressure signal, the cerebral autoregulation data, the confidence level, the activity metric, etc.), instructions (e.g., software or firmware for processing the EEG signal, the regional oxygen saturation signal, the blood pressure signal, and/or the cerebral autoregulation data, for determining the DOCx, the regional oxygen saturation value, the confidence level, and/or the cerebral autoregulation status, and/or taking appropriate remedial actions), predetermined thresholds, and any other suitable data.

The techniques presented and claimed herein are referenced and applied to material objects and concrete examples of a practical nature that demonstrably improve the present technical field and, as such, are not abstract, intangible, or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, combinations, and alternatives falling within the spirit and scope of the disclosure as defined by the following appended claims.

What is claimed is:

1. An electroencephalography (EEG) monitor, comprising:
 a memory encoding one or more processor-executable routines; and
 one or more processors configured to access and execute the one or more processor-executable routines encoded by the memory, wherein the one or more processor-executable routines, when executed, cause the one or more processors to:
  receive electroencephalography (EEG) data from an EEG sensor configured to acquire the EEG data from a patient;
  determine a depth of consciousness index for the patient based on the EEG data, wherein the depth of consciousness index is indicative of a level of consciousness of the patient under general anesthesia;
  determine a regional oxygen saturation value of the patient based on regional oximetry data;
  determine a value of a Pearson correlation coefficient for the regional oxygen saturation value and the depth of consciousness index over a predetermined period of time, wherein the value of the Pearson correlation coefficient is indicative of a correlation between the regional oxygen saturation value and the depth of consciousness index;

determine a confidence level for the depth of consciousness index based at least in part on the value of the Pearson correlation coefficient, wherein the one or more processors are configured to determine that the confidence level is a first confidence level when the value of the Pearson correlation coefficient is negative and a second confidence level when the value of the Pearson correlation coefficient is positive, wherein the confidence level is indicative of a reliability of the depth of consciousness index, and wherein the first confidence level represents a higher confidence level than the second confidence level; and provide the depth of consciousness index and the confidence level to an output device for display of the depth of consciousness index and the confidence level.

2. The EEG monitor of claim 1, wherein the one or more processor-executable routines, when executed, cause the one or more processors to receive the regional oximetry data from a regional oximetry sensor operatively coupled to the EEG monitor or from a regional oximetry monitor operatively coupled to the EEG monitor.

3. The EEG monitor of claim 1, wherein the predetermined period of time occurs during induction of anesthesia when one or more anesthetic agents are provided to the patient to reduce the level of consciousness of the patient.

4. The EEG monitor of claim 1, wherein the memory stores a look-up table comprising a plurality of values of the Pearson correlation coefficient, wherein each value of the plurality of values of the Pearson correlation coefficient is associated with a confidence level, and wherein the one or more processor-executable routines, when executed, cause the one or more processors to access the look-up table using the value of the Pearson correlation coefficient to determine the confidence level.

5. The EEG monitor of claim 1, wherein the one or more processor-executable routines, when executed, cause the one or more processors to:

determine a stage of general anesthesia from a plurality of stages of general anesthesia during which the predetermined period of time occurs, wherein the plurality of stages of general anesthesia comprise an anesthesia induction stage, an anesthesia maintenance stage, and an anesthesia emergence stage; and determine the confidence level based on the value of the Pearson correlation coefficient and the stage of general anesthesia.

6. The EEG monitor of claim 5, wherein the one or more processor-executable routines, when executed, cause the one or more processors to:

determine the first confidence level for the depth of consciousness index when the value of the Pearson correlation coefficient is negative and the stage of general anesthesia is the anesthesia induction stage; and determine the second confidence level for the depth of consciousness index when the value of the Pearson correlation coefficient is positive and the stage of general anesthesia is the anesthesia induction stage.

7. The EEG monitor of claim 1, wherein the one or more processor-executable routines, when executed, cause the one or more processors to:

determine a cerebral autoregulation status for the patient based on cerebral autoregulation data; and adjust the confidence level based at least in part upon the cerebral autoregulation status.

8. The EEG monitor of claim 7, wherein the one or more processor-executable routines, when executed, cause the one or more processors to:

determine cerebral autoregulation for the patient is impaired based on the cerebral autoregulation status; and decrease the confidence level in response to a determination that cerebral autoregulation is impaired.

9. A method comprising:

determining, by one or more processors, a depth of consciousness index for a patient based on electroencephalography (EEG) data, wherein the depth of consciousness index is indicative of a level of consciousness of the patient under general anesthesia;

determining, by the one or more processors, a regional oxygen saturation for the patient based on regional oximetry data;

determining, by the one or more processors, a value of a Pearson correlation coefficient for the regional oxygen saturation value and the depth of consciousness index over a predetermined period of time, wherein the value of the Pearson correlation coefficient is indicative of a correlation between the regional oxygen saturation value and the depth of consciousness index;

determining, by the one or more processors, a confidence level for the depth of consciousness index based at least in part on the value of the Pearson correlation coefficient, wherein determining the confidence level comprises determining that the confidence level is a first confidence level when the value of the Pearson correlation coefficient is negative and a second confidence level when the value of the Pearson correlation coefficient is positive, wherein the confidence level is indicative of a reliability of the depth of consciousness index, and wherein the first confidence level represents a higher confidence level than the second confidence level; and causing, by the one or more processors, an output device to present the depth of consciousness index and the confidence level.

10. The method of claim 9, further comprising:

determining, by the one or more processors, a cerebral autoregulation status based on cerebral autoregulation data; and causing, by the one or more processors, the output device to output an alarm signal if the cerebral autoregulation status indicates that the cerebral autoregulation of the patient is impaired.

11. A system comprising:

a display; and one or more processors configured to:

receive electroencephalography (EEG) data of a patient;

determine a depth of consciousness index for the patient based on the EEG data, wherein the depth of consciousness index is indicative of a level of consciousness of the patient under general anesthesia;

determine a regional oxygen saturation value for the patient based on regional oximetry data;

determine a value of a Pearson correlation coefficient for the regional oxygen saturation value and the depth of consciousness index over a predetermined period of time;

determine a confidence level for the depth of consciousness index, wherein the one or more processors are configured to determine that the confidence level is a first confidence level when the value of the Pearson correlation coefficient is negative and a second confidence level when the value of the Pearson correlation coefficient is positive, wherein the confidence level is indicative of a reliability of the depth of consciousness index, and wherein the first confidence level represents a higher confidence level than the second confidence level; and present the depth of consciousness index and the confidence level via the display.

12. The system of claim 11, further comprising:
an EEG sensor configured to acquire the EEG data from the patient; and
a regional oximetry sensor configured to acquire the regional oximetry data from the patient.

13. The system of claim 11, further comprising a memory storing information associating each value of a plurality of values of the Pearson correlation coefficient with a confidence level, wherein the one or more processors are configured to determine the confidence level based on the information.

14. The system of claim 11, wherein to determine the confidence level, the one or more processors are configured to:
determine a stage of general anesthesia from a plurality of stages of general anesthesia during which the predetermined period of time occurs, wherein the plurality of stages of general anesthesia comprise an anesthesia induction stage, an anesthesia maintenance stage, and an anesthesia emergence stage, and
determine the confidence level based on the value of the Pearson correlation coefficient and the stage of general anesthesia.

15. The system of claim 11, wherein the one or more processors are configured to:
determine a cerebral autoregulation status for the patient based on cerebral autoregulation data, and
adjust the confidence level based at least in part upon the cerebral autoregulation status.

* * * * *